(12) United States Patent
Hong et al.

(10) Patent No.: US 7,759,391 B2
(45) Date of Patent: Jul. 20, 2010

(54) PHARMACEUTICAL COMPOSITION COMPRISING THIACREMONONE FOR TREATING COLON CANCER

(75) Inventors: Jin Tae Hong, Chungbuk (KR); Jung Ok Ban, Chungbuk (KR); Heon-Sang Jeong, Chungbuk (KR); Dae Joong Kim, Chungbuk (KR)

(73) Assignee: Chungbuk National University Industry Academic Cooperation Foundation, Chungbuk (KR)

( * ) Notice: Subject to any disclaimer, the term of this patent is extended or adjusted under 35 U.S.C. 154(b) by 0 days.

(21) Appl. No.: 12/186,534

(22) Filed: Aug. 6, 2008

(65) Prior Publication Data

US 2009/0093536 A1    Apr. 9, 2009

(30) Foreign Application Priority Data

Oct. 8, 2007    (KR)    .................. 10-2007-0100998

(51) Int. Cl.
*A61K 31/381*    (2006.01)
(52) U.S. Cl. ...................................... 514/445
(58) Field of Classification Search .................. 514/445
See application file for complete search history.

(56) References Cited

U.S. PATENT DOCUMENTS

2007/0122497 A1*   5/2007   Managoli .................... 424/725

FOREIGN PATENT DOCUMENTS

WO    WO 2004/069262 A1 *   8/2004

OTHER PUBLICATIONS

Sausville et al. Cancer Research, 2006, vol. 66, pp. 3351-3354.*
Johnson et al. British J. of Cancer, 2001, 84(10):1424-1431.*
Lamm et al. J. Nutr., 2001, vol. 131, pp. 1067S-1070S.*
Gehrt et al. Natural Product Letters, 2000, vol. 14, No. 4, pp. 281-284.*
Xiao et al., "Effects of a series of organosulfur compounds on mitotic arrest and induction of apoptosis in colon cancer cells." Mol Cancer Ther 2005;4(9). Sep. 2005.
Teyssier et al., "Metabolism of Dipropyl Disulfide by Rat Liver Phase I and Phase II Enzymes and by Isolated Perfused Rat Liver." DMD 28:648-654, 2000 (Feb. 22, 2000).
Ban et al., "Inhibition of Cell Growth and Induction of Apoptosis via Inactivation of NF-κB by a Sulfurcompound Isolated From Garlic in Human Colon Cancer Cells." J Pharmacol Sci 104, 374-383 (Aug. 2007).

* cited by examiner

*Primary Examiner*—James D Anderson
(74) *Attorney, Agent, or Firm*—The Nath Law Group; Joshua B. Goldberg; Mih Suhn Koh

(57) ABSTRACT

The present invention relates to an anti-cancer composition, which comprises a sulfur-containing compound thiacremonone as an active ingredient. The active ingredient induces the death of cancer cells by apoptosis through the action of specific inhibition of the activity of NF-κB. The composition can be effectively used in the treatment or prevention of cancer.

1 Claim, 10 Drawing Sheets

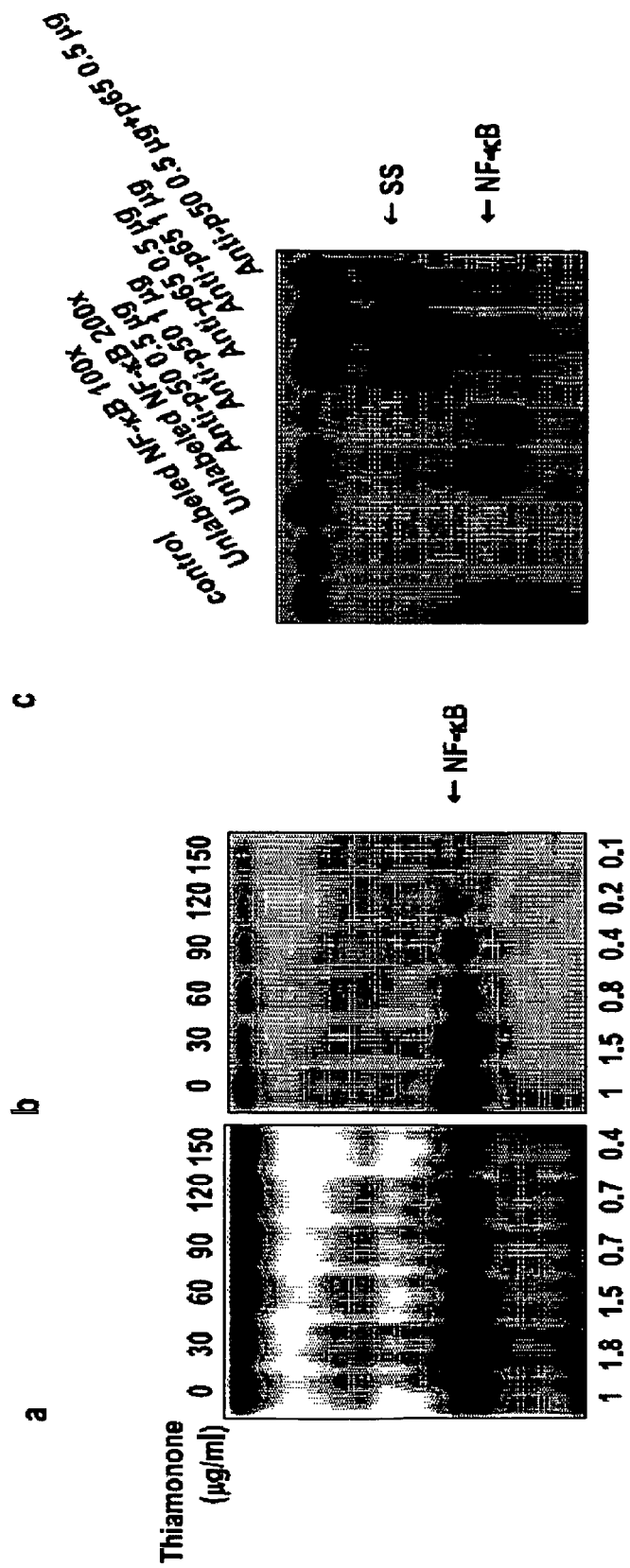

a b a b a b a b

US 7,759,391 B2

PHARMACEUTICAL COMPOSITION COMPRISING THIACREMONONE FOR TREATING COLON CANCER

CROSS-REFERENCE TO RELATED APPLICATION

The benefit of priority is claimed to Republic of Korea patent application number 10-2007-0100998 filed Oct. 8, 2007, which is incorporated by reference herein.

INTRODUCTION

The present invention relates to a composition for preventing or treating cancer comprising thiacremonone as an active ingredient.

BACKGROUND

The role of dietary compounds in cancer prevention and treatment has been widely discussed (1-3). In this regard, the potential chemopreventive effect of garlic has been of interest since garlic contains numerous pharmacologically active substances including sulfur and selenocompounds that have been shown to alter the activation of several carcinogens and to inhibit cancer cell growth and/or to induce cell death (4-6). Sulfur compounds such as diallyl sulfide, S-allylmercaptocysteine, and ajoene isolated from garlic have been known to increase the activity of enzymes involved in the metabolism of carcinogens (7) and have anti-oxidant activities (8) and protective activities against lipid peroxidation and hepato toxicity in vitro and in vivo (9, 10).

Several recent studies showed that these sulfur compounds are able to inhibit the growth of several human cancer cells including breast (MCF-7), hepatoma (HepG2), and lymphocytic leukemia as well as lung cancer cells (NSCLC) in culture (11-14). In addition, the importance of sulfur compounds in the preventative effect against colon cancer development has been demonstrated by several research groups (15-17). Jakubikova and Sedlak reported that organosulfides derived from garlic induced apoptotic cell death of human colon carcinoma cell lines (15). Garlic containing sulfur compounds has also been demonstrated to prevent chemical-induced rat aberrant crypt formation (16) and colon cancer incidence (17). Even though sulfur compounds from natural products have been demonstrated as chemopreventive agents, their molecular mechanisms are not fully demonstrated.

Recent evidences indicate that nuclear transcription factor-κB (NF-κB) activation has been connected with multiple aspects of oncogenesis, including the control of apoptosis, proliferation, differentiation, and migration of the cells (18-20). An association of colorectal cancer development and activation of NF-κB has been demonstrated. NF-κB activities were increased in the colon cancer cell lines and human tumor samples as well as nucleic of stromal macropharges in sporadic adenomatous polyps (21, 22). NF-κB can lead to further proliferation of transformed cells through enhanced production of growth factors and cytokines (23). Thus, an inactivation of NF-κB in many cancer cells by a chemotherapeutic agent has been demonstrated to blunt the ability of the cancer cells to grow by the antiapoptotic function of NF-κB in mammalian cells (24-27). Although many compounds have been identified from garlic (28, 29) and their anticancer activities (4-6) have been demonstrated, new compounds and action mechanisms underlying their anticancer effects have been not fully studied.

Throughout this application, various patents and publications are referenced, and citations are provided in parentheses. The disclosure of these patents and publications in their entities are hereby incorporated by reference into this application.

SUMMARY

The present inventors have performed intensive research to discover novel compounds exhibiting anti-cancer activity from natural products. As a result, we have verified that the sulfur containing compound, thiacremonone, which has been isolated from garlic, specifically inhibits the activity of NF-κB in cancer cells so that it exhibits an anti-cancer activity by inducing the cancer cell death through apoptosis.

Accordingly it is an object of this invention to provide a pharmaceutical composition for treating or preventing cancer comprising thiacremonone as an active ingredient.

It is another object of this invention to provide a food composition for treating, preventing or relieving cancer comprising thiacremonone as an active ingredient.

It is still another object of this invention to provide a method for preventing or treating cancer, which comprises administering to a subject suffering from cancer a pharmaceutical composition comprising (a) a pharmaceutically effective amount of thiacremonone; and (b) a pharmaceutically acceptable carrier.

Other objects and advantages of the present invention will become apparent from the detailed description to follow taken in conjugation with the appended claims and drawings.

BRIEF DESCRIPTION OF THE DRAWINGS

FIGS. 1A and 1B show the effect of thiacremonone on NF-κB activation in SW620 and HCT116 colon cancer cells.

FIG. 1A: Nuclear extract from SW620 (panel a) and HCT116 (panel b) colon cancer cells treated with thiacremonone (30-150 μg/ml) for 1 h was incubated in binding reactions of $^{32}P$-end-labeled oligonucleotide containing the κB sequence. The activation of NF-κB was investigated using EMSA as described in Materials and Methods. For competition assays, nuclear extracts from cells treated with TNF-α were incubated for 1 h before EMSA with unlabled NF-κB oligonucleotide or labeled NF-κB oligonucleotide. For supershift assays, nuclear extracts from cells treated with TNF-α were incubated for 1 h before EMSA with specific antibodies against the p50 and p65 NF-κB isoforms. SS indicates supershift assay using p65 antibody (panel c). Quantification of band intensities from three independent experimental results performed by densitometry (Imaging System) and the value under each band indicated as fold difference from the untreated control group.

FIG. 1B: Colon cancer cells were transfected with pNF-κB-Luc plasmid (5×NF-κB) and then activated with TNF-α (150 U/ml) alone or TNF-α plus different concentrations (30-150 μg/ml) of thiacremonone at 37° C. in both SW620 (panel a and b) and HCT116 (panel c and d) colon cancer cells, and then the luciferase activity was determined. All values represent mean±S.D. of three independent experiments performed in triplicate. RLU is relative to luciferase activity in transfected unstimulated cells. *P<0.05 indicates statistically significant differences from the TNF-α-treated group.

Figure 2A:
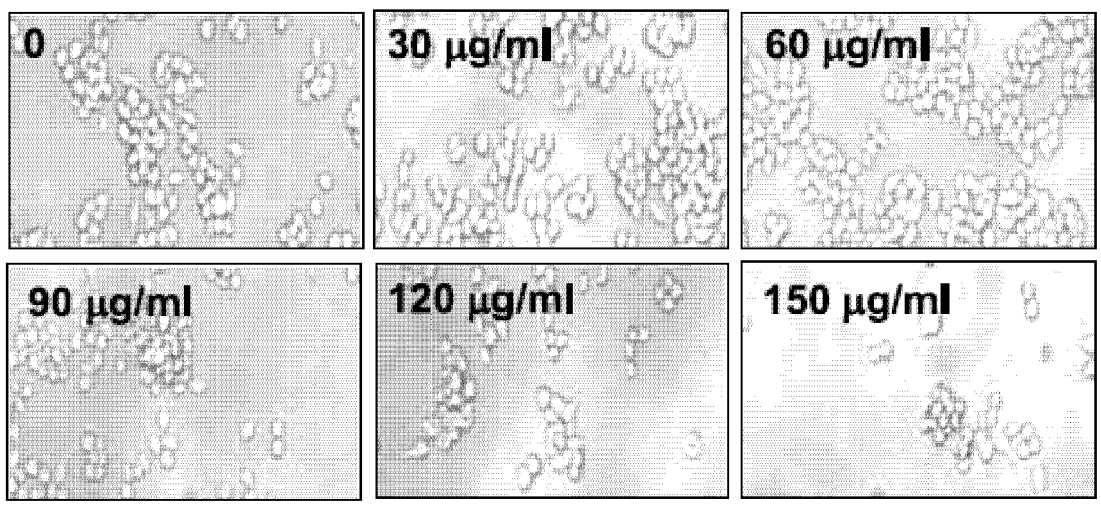
FIGS. 2A-2C demonstrate morphological changes and cell viability of colon cancer and normal cells by thiacremonone.
Figure 2A:
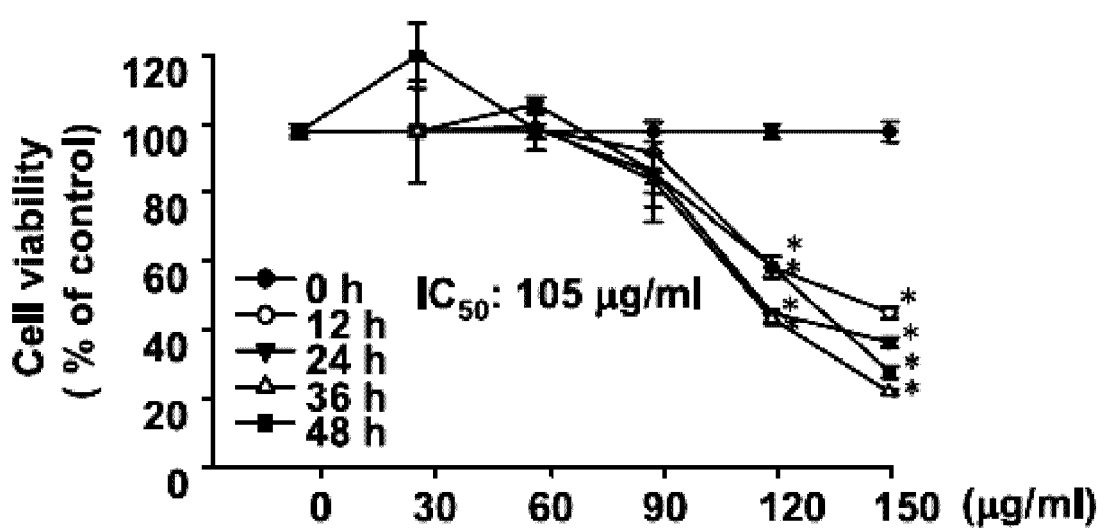
Figure 2B:
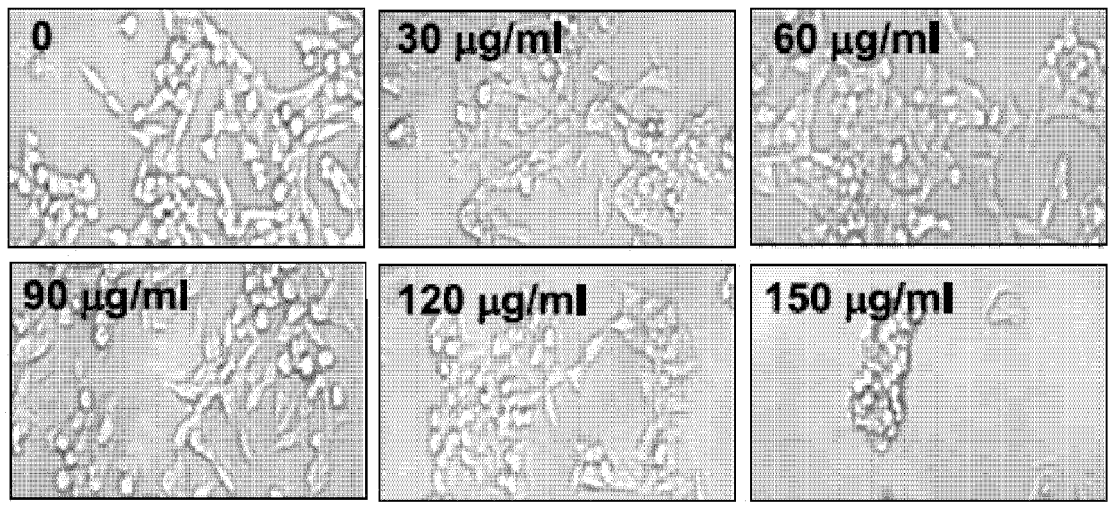
Figure 2B:
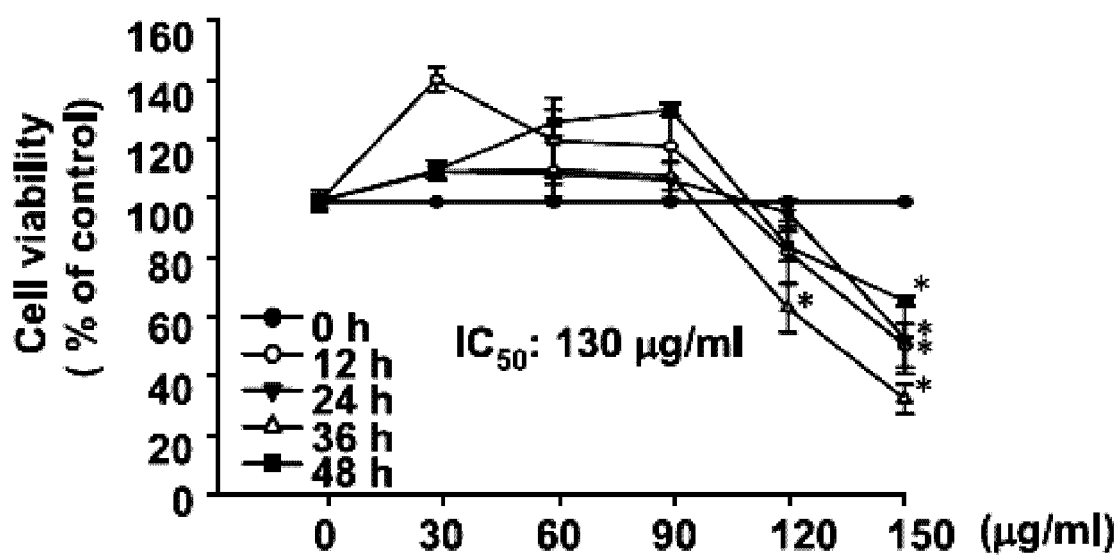
Figure 2C:
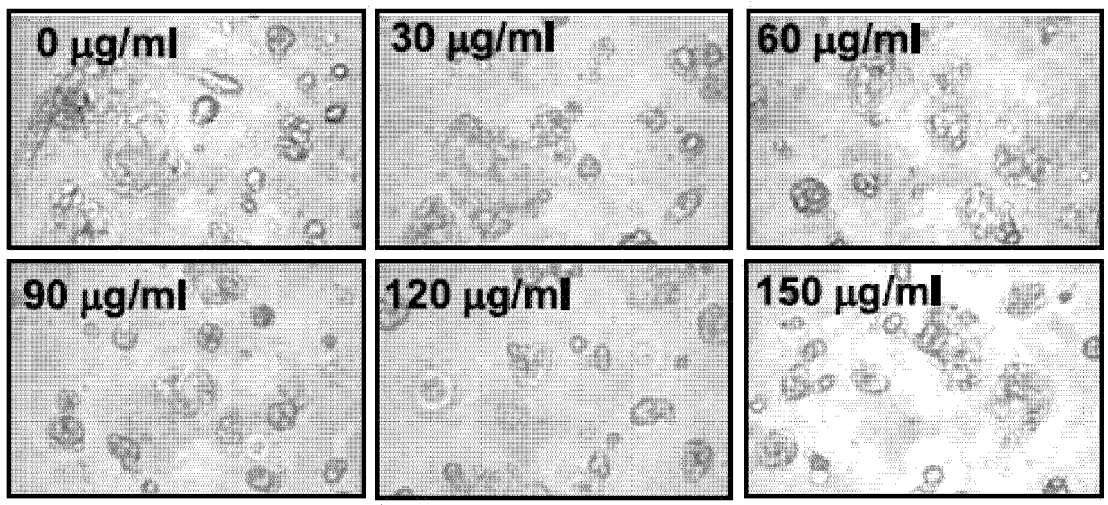
Figure 2C:
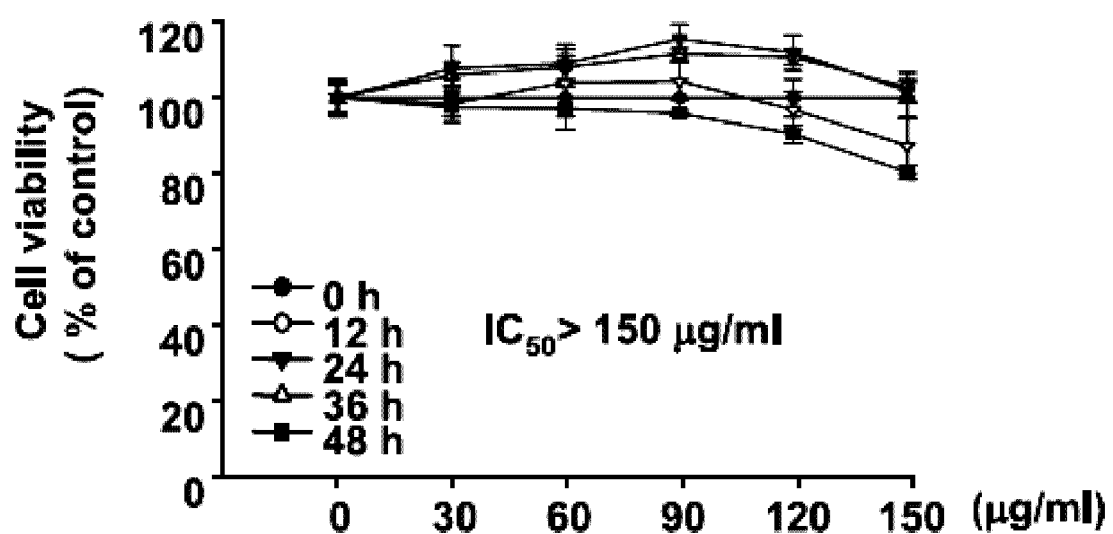

Panel a of FIGS. 2A-2C: Morphorogical changes were observed under a microscope (magnification, ×200). SW620 (FIG. 2A) and HCT116 (FIG. 2B) colon cancer cells and normal cells (Caco-2) (FIG. 2C) were treated with various doses (30-150 μg/ml) of thiacremonone for 24 h.

Panel b of FIGS. 2A-2C: Cell viability was determined by CCK-8 assay as described in Materials and Methods. SW620 (FIG. 2A) and HCT116 (FIG. 2B) colon cancer cells as well as normal cells (Caco-2) (FIG. 2C) were treated with various doses (30-150 μg/ml) of thiacremonone for different times (12-48 h). Values are each the mean±S.D. of three experiments, each performed in triplicate.

Figure 3A:
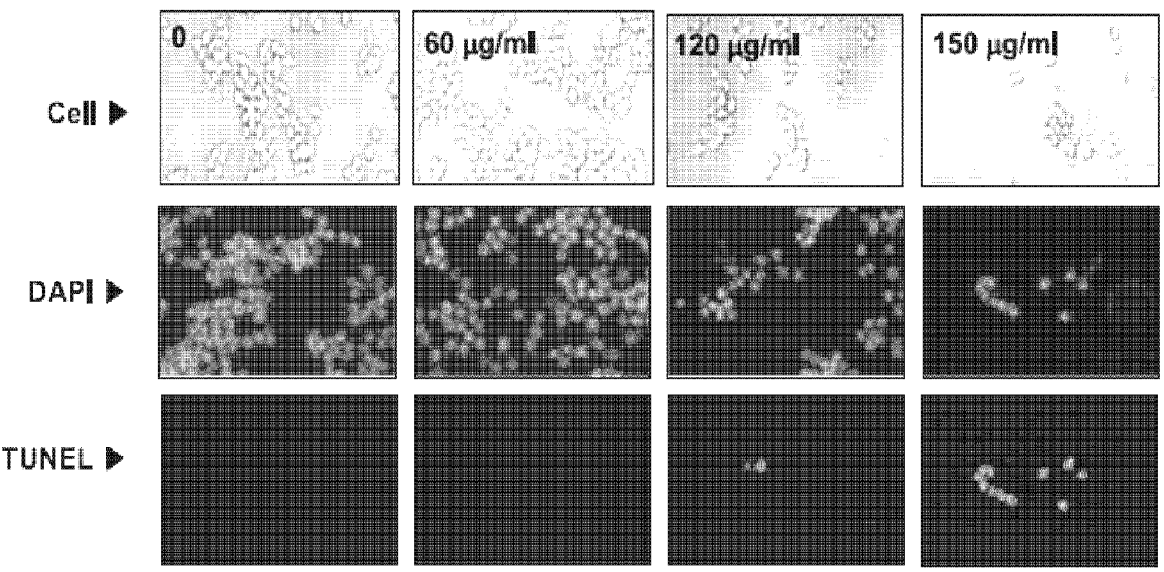
Figure 3A:
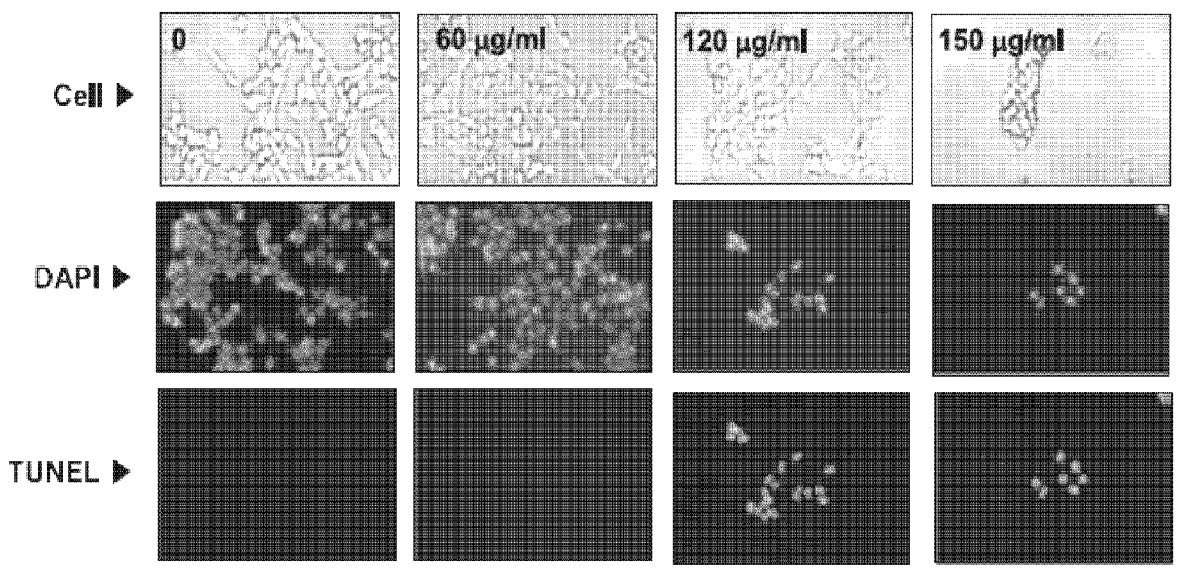
Figure 3B:
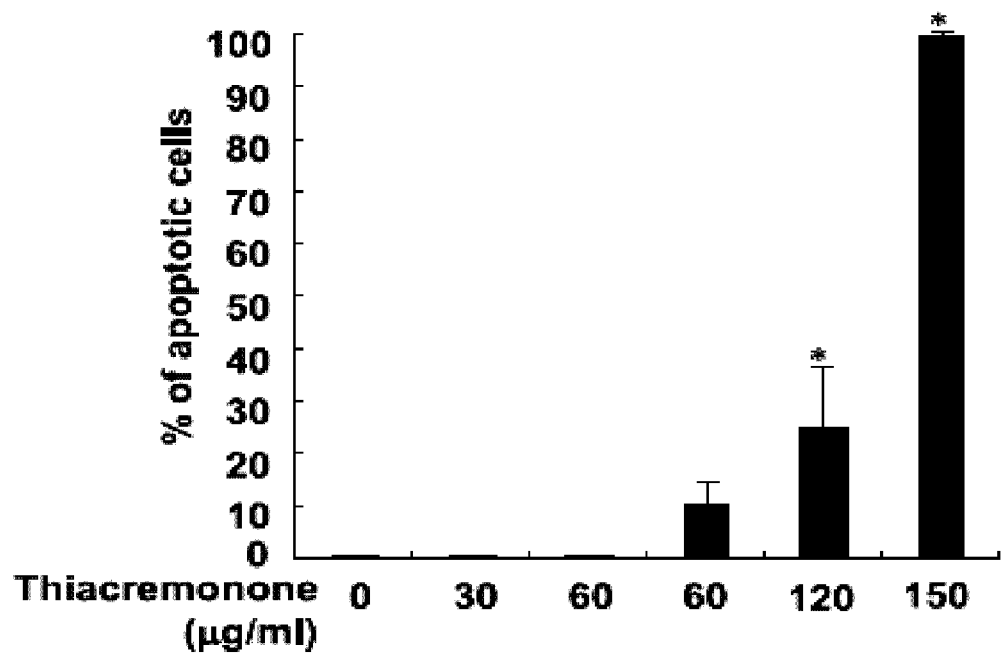
Figure 3B:
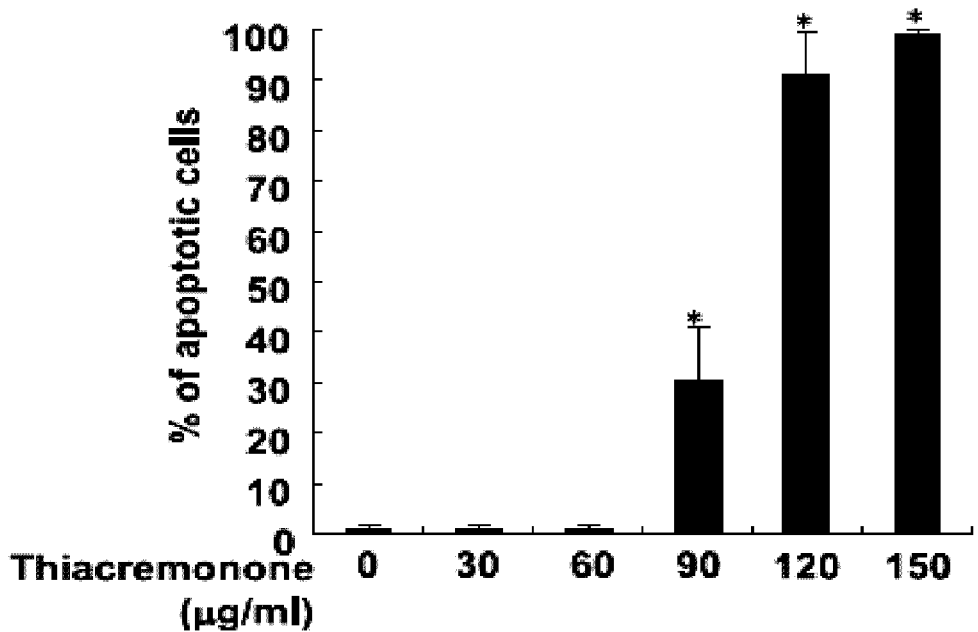

FIGS. 3A and 3B represent morphological changes and apoptotic cell death of SW620 (panel a) and HCT116 (panel b) colon cancer cells by thiacremonone.

FIG. 3A: SW620 and HCT116 colon cancer cells were treated with various doses (30-150 µg/ml) of thiacremonone for 24 h. Cell morphological changes were observed under a microscope (upper panels; magnification, ×200) and apoptotic cells were examined by fluorescence microscopy after TUNEL staining (fluorescent microscopy magnification, ×200) (lower panels). Total number of cells in a given area was determined by DAPI nuclear staining (fluorescent microscopy magnification, ×200) (middle panels).

FIG. 3B: The apoptotic index was determined as the DAPI-stained TUNEL-positive cell number counted. Values are mean±S.E.M. of three experiments, each performed in triplicate. *P<0.05 indicates statistically significant differences from the untreated group.

Figure 4:
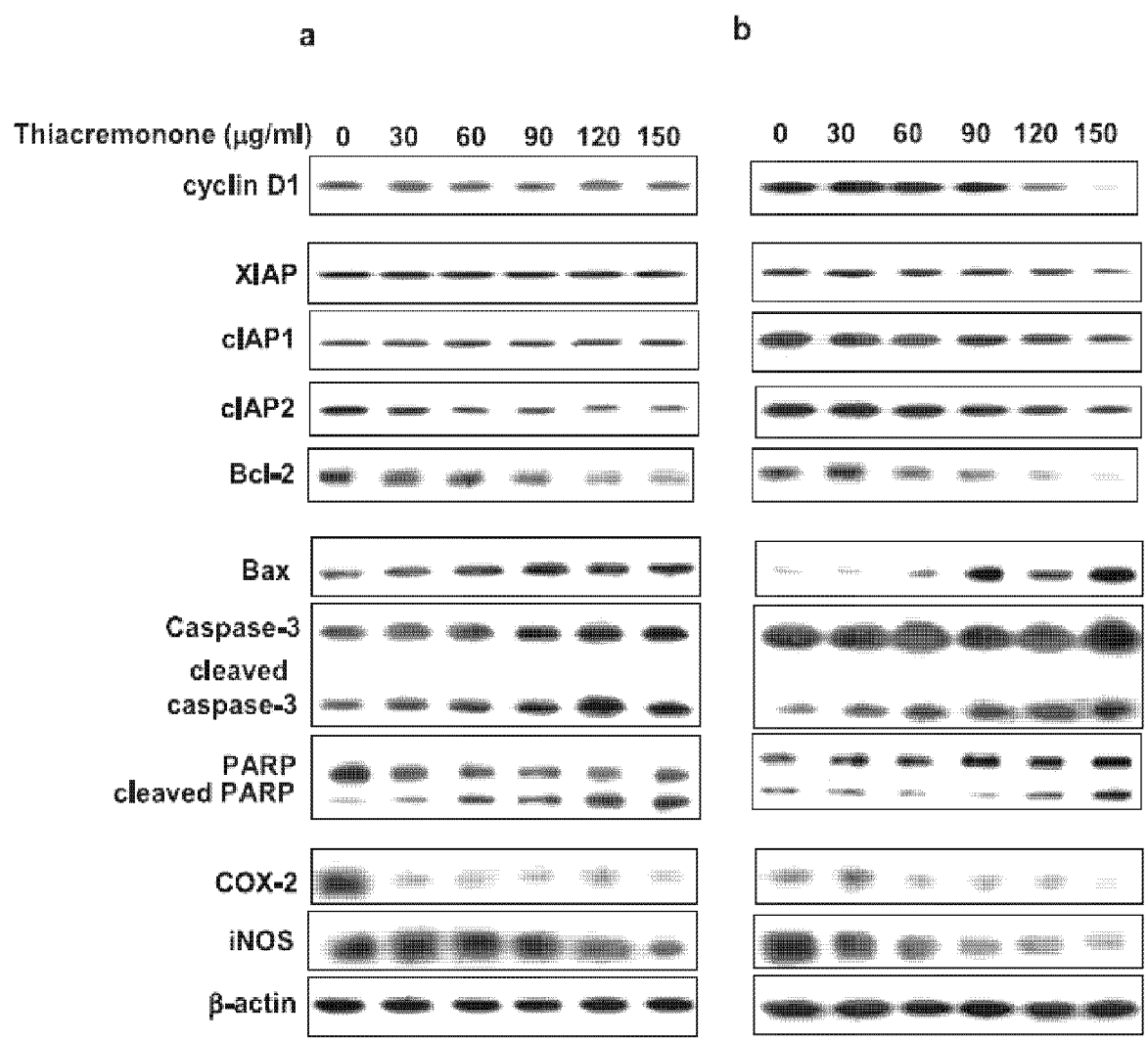

FIG. 4 shows the effect of thiacremonone on expression of apoptosis regulatory proteins. The cells were treated with different concentrations (30-150 µg/ml) of thiacremonone at 37° C. for 24 h. Equal amounts of total proteins (50 µg/lane) were subjected to 12% SDS-PAGE. Expressions of Bax, cleaved caspase-3, cleaved PARP, Bcl-2, cIAP1/2, XIAP, and β-actin were detected by western blotting using specific antibodies. β-Actin protein was used an internal control. Panel a: SW620 colon cancer cells. Panel b: HCT116 colon cancer cells. Each band is representative of three independent experiments.

Figure 5:
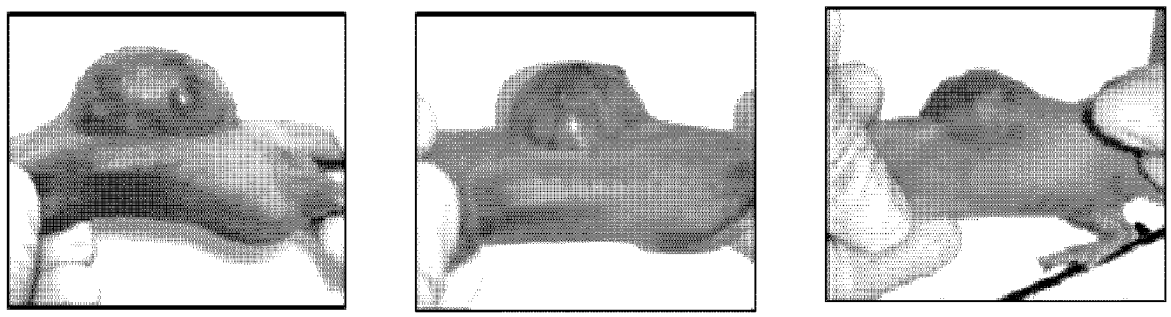
Figure 5:
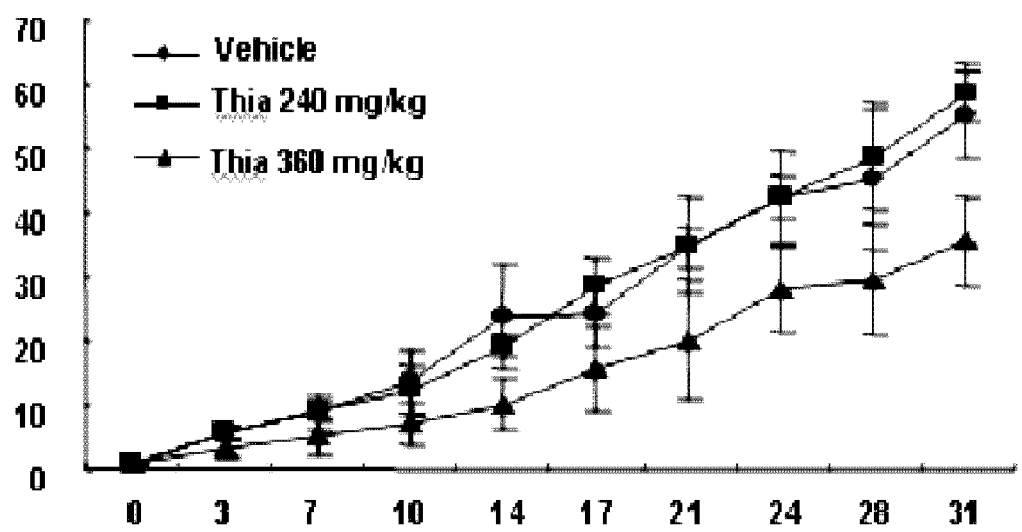

FIG. 5 represents the relative tumor growth delay measured after treatment of thiacremonone (240 and 360 mg/kg for four weeks, n=10) in comparison with the sham control group (saline). By day 31, tumor volume in mice treated with thiacremonone 240 mg/kg and 360 mg/kg were reduced to 92.5% and 59.1% of sham control group, respectively. These results suggested that in agree with in vitro, thiacremonone suppressed cancer cell growth in vivo.

Figure 6:
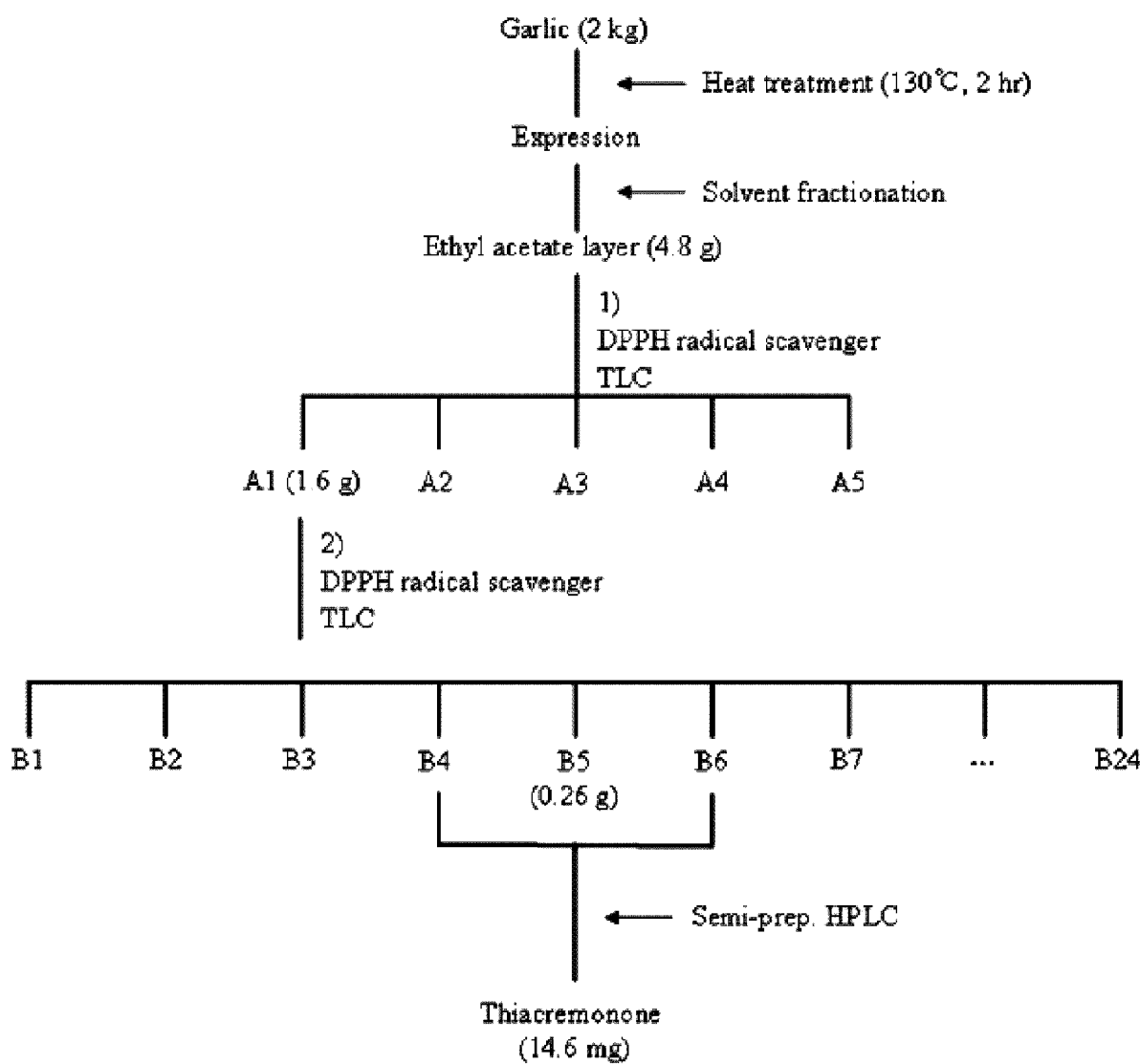

FIG. 6 shows extraction scheme for the isolation of active compound from heated garlic (*Allium sativum* L.) at 130° C. for 2 hr. Silica gel column chromatography: dichloromethane: methanol=20/1, 10/1, 5/1, 1/1, 0/1, v/v.

DETAILED DESCRIPTION

In one aspect of this invention, there is provided a composition for treating or preventing cancer comprising a sulfur-containing compound thiacremonone of the formula I as an active ingredient.

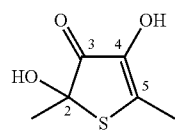

(I)

In another aspect of this invention, there is provides a method for preventing or treating cancer, which comprises administering to a subject suffering from cancer a pharmaceutical composition comprising (a) a pharmaceutically effective amount of thiacremonone; and (b) a pharmaceutically acceptable carrier.

The present inventors have made intensive researches in order to find out novel compounds exhibiting anti-cancer activities from natural products. As a result, the inventors have verified that the sulfur containing compound, thiacremonone, which has been isolated from garlic, specifically inhibits the activity of NF-κB in cancer cells so that it exhibits anti-cancer activities by inducing the cancer cell death through apoptosis.

Thiacremonone(2,4-dihydroxy-2,5-dimethyl-thiophene-3-one), the active ingredient of the present composition, is a sulfur-containing compound isolated and purified from the fractions exhibiting anti-oxidation activities fractionated from heated garlic (*Allium sativum* L.). Thiacremonone is a compound, which has been known to be produced by *Acremonium* sp. Strain HA33-95 as described by Gehrt et al. (31). In addition, it has been also reported that thiacremonone can induce the differentiation of animal cells.

The instant invention provides a novel use of thiacremonone for treating, preventing or relieving cancer. The active ingredient of the present composition specifically inhibits the activity of NF-κB in cancer cells so that it can induce cancer cell death through apoptosis without affecting normal cells. Accordingly the composition of this invention can be used as an effective anti-cancer agent.

According to a preferred embodiment, the present invention provides a pharmaceutical composition for preventing or treating cancer comprising (a) a pharmaceutically effective amount of thiacremonone; and (b) a pharmaceutically acceptable carrier.

The term "cancer" used herein means a group of diseases in which cells are aggressive (i.e., grow and divide without respect to normal limits), invasive (i.e., invade and destroy adjacent tissues), and/or metastatic (i.e., spread to other locations in the body). The terms "cancer" and "malignant tumor" can be used interchangeably herein.

The cancer treated, prevented or relieved by the instant pharmaceutical composition includes breast cancer, lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, small intestine cancer, endocrine cancer, thyroid cancer, parathyroid cancer, adrenal cancer, soft tissue tumor, urethral cancer, prostate cancer, bronchogenic cancer, bone marrow tumor, but not limited to. Preferably, the present composition can be used to treat or prevent colon cancer.

The term "preventing" used herein refers to preventing a disease, disorder or condition from occurring in an animal that may be predisposed to the disease, disorder and/or condition, but has not yet been diagnosed as having it. The term "treating" used herein refers to: (i) inhibiting the disease, disorder or condition, i.e., arresting its development; (ii) relieving the disease, disorder or condition, i.e. causing regression of disease, disorder and/or condition; and (iii) removing or eliminating the disease, disorder or condition.

In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Preferably, the pharmaceutical composition of the present invention is administered with a daily dose of 0.001-1000 mg/kg (body weight).

The pharmaceutical composition of this invention may be administered via oral or parenteral route. If the administration of the present composition is done via parenteral route, it may be administered by any convenient route, for example by intravenous, subcutaneous, intramuscular, intraperitoneal, and intradermal routes. The administration route of the pharmaceutical composition of this invention may be selected according to the type of cancer.

The concentration of thiacremonone in the instant pharmaceutical composition is not limited to the specific range and may be selected according to the object of treatment, the patient's condition, period of need and the severity of the disease.

According to the conventional techniques known to those skilled in the art, the pharmaceutical composition may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The present composition for treating, preventing, or relieving cancer may be prepared to provide a food composition, in particular a health food composition. The food composition may comprise conventional additives for preparing food compositions, e.g., proteins, carbohydrates, lipids, nutritive substances and flavors. For example, where the food composition of this invention is provided as a drink, it may further comprise flavors and natural carbohydrates as well as lactic acid bacteria and collagen as active ingredients. Non-limiting examples of natural carbohydrates include, but not limited to, monosaccharide (e.g., glucose and fructose), disaccharide (e.g., maltose and sucrose), oligosaccharide, polysaccharide (e.g., dextrin and cyclodextrin) and sugar alcohol (e.g., xylitol, sorbitol and erythritol). Non-limiting examples of flavors include, but not limited to, natural flavors (e.g., thaumatin and extract of *Stevia*) and synthetic flavors (e.g., saccharin and aspartame). Considering availability to foods, the food composition of this invention is very useful in preventing or treating cancer.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Sample Preparation

Garlic, *Allium sativum* L., was purchased from the Chungbuk Agriculture and Marine Products Market in June 2006 and stored at −20° C. Heat treatment was performed using a temperature- and pressure-controlling apparatus (Jisico, Seoul, Korea). The samples were heated at temperatures of 120° C., 130° C., and 140° C. for 2 hr. The heated samples were juiced and then filtered through No. 2 Whatman filter paper on a Büchner funnel under a vacuum. The garlic juice was kept at −20° C. until analysis.

Selection of the Solvent Layer

Heated garlic juice (HGJ) was partitioned consecutively in a separating funnel using solvents of increasing polarity: n-hexane, chloroform, ethyl acetate, butanol, and water. The solvent was evaporated using a rotary evaporator (Eyela N-1000, Tokyo, Japan) at 40° C. The dried residues of the five extracts were measured for 1,1-diphenyl-2-picrylhydrazyl (DPPH) radical scavenging activity and 2,2'-azino-bis(3-ethylbenzthiazoline-6-sulfonic acid) (ABTS) radical cation scavenging activity.

DPPH Radical Scavenging Activity

The DPPH radical scavenging activity of the extracts, fractions, and isolated compound, based on the scavenging activity of the stable DPPH free radical, was measured according to the method of Bektas et al. (18), with some modifications. Aliquots of 0.8 mL of 0.2 mM DPPH (Sigma-Aldrich, St. Louis, Mo., USA) methanolic solution were mixed with 0.2 mL of the extracts. The mixture was shaken vigorously and then left to stand for 30 min under low light. The absorbance was measured at 520 nm using a spectrophotometer (DU 650; Beckman, Fullerton, Calif., USA). The percentage inhibition of activity was calculated as $(A_0-A_1)/A_0 \times 100$, where $A_0$ is the absorbance without the sample and $A_1$ is the absorbance with the sample. Sample concentrations providing the 50% inhibition concentration ($IC_{50}$) were calculated from a graph of inhibition percentage versus sample concentration. All samples were analyzed in triplicate.

ABTS Radical Scavenging Activity

The ABTS radical cation scavenging activity of the extracts and fractions was measured according to the method of Roberta et al. (19) and Kim et al. (20), with some modifications. The ABTS radical cation was generated by adding 7 mM ABTS to 2.45 mM potassium persulfate solution and leaving the mixture to stand overnight in the dark at room temperature. The ABTS radical cation solution was diluted with distilled water to obtain an absorbance of 1.4-1.5 at 735 nm. A 1 mL aliquot of diluted ABTS radical cation solution was added to 50 µL of the extract, fractions, ascorbic acid standard solution, or distilled water. The absorbance at 735 nm was determined using a spectrophotometer (DU 650; Beckman, Fullerton, Calif., USA) after 60 min. The ascorbic acid equivalent antioxidant activity (AEAC) was calculated as $(\Delta A/\Delta A_{AA}) \times C_{AA}$, where $\Delta A$ is the change in absorbance after the addition of the sample, $\Delta A_{AA}$ is the change in absorbance after the addition of ascorbic acid standard solution, and $C_{AA}$ is the concentration of the ascorbic acid standard solution. The ABTS radical cation scavenging activity was expressed as the AEAC in milligrams of ascorbic acid equivalents. All samples were analyzed in triplicate.

Thin Layer Chromatography (TLC)

Analytical TLC of extracts, fractions, and the isolated compound was performed using silica gel 60 F254 glass plates (0.25 mm thick, 20×20 cm; Merck, Darmstadt, Germany), which were developed using appropriate solvents for each sample, i.e., dichloromethane:methanol mixtures in different ratios. The resultant bands were located using ultraviolet (UV) light (254 and 365 nm) and 20% sulfuric acid solution in 10% vanillin/ethanol spray, followed by heating in an oven for about 10 min at 110° C. For the qualitative detection of radical scavenging compounds, the TLC plates were sprayed with 1 mM methanol solution of DPPH, which produced yellow spots on a purple background.

Open Column Chromatography

Isolation of the active compound from the ethyl acetate layer of HGJ treated at 130° C. for 2 hr was subjected to column chromatography on silica gel. HGJ (2 kg) was partitioned consecutively using various solvents. The ethyl acetate extract (4.8 g) was subjected to open-column (500×35 mm, i.d.) chromatography using silica gel (Kiesel gel 60, 70-230 mesh; Merck); elution was carried out using a mixture of dichloromethane:methanol with an increasing amount of methanol (20:1, 10:1, 5:1, 1:1, 0:1, v/v). Five fractions were collected and assayed for antioxidant activity or used for TLC by pooling them into one major fraction, A1. The active fraction A1 (1.6 g) was subjected to further open-column (300×10 mm, i.d.) chromatography using silica gel; elution was carried out using a mixture of dichloromethane:methanol with increasing amounts of methanol (20:1, 10:1, 5:1, 1:1, 0:1, v/v). A total of 24 fractions was collected and assayed for antioxidant activity or used for TLC by pooling them into four major fractions, B4-B6 (0.26 g). The removal of solvents from fractions was performed using a rotary evaporator at 40° C.

Semi-Preparative HPLC

The active fractions B4-B6 were purified by preparative RP-HPLC (Discovery® C18 column; 250×10 mm, i.d., 5 μm, Supelco, Bellefonte, USA) on a Younglin SP930D instrument (Younglin Instrument, Anyang, Korea) equipped with a UV detector, operating at 365 nm, at room temperature and a flow rate of 3.5 mL/min. The elution gradient was a water:acetonitrile phase at 95:5 (v/v) for the first 11 min, followed by a continuous change from 95:5 to 50:50 over the next 29 min. The pure compound was obtained after evaporating the solvents using a rotary evaporator.

Structural Identification of the Isolated Compound

The structure of the purified compound was determined using several spectroscopic methods. The UV spectrum in methanol was recorded on a spectrophotometer (UV-1650; Shimadzu, Kyoto, Japan). The infrared (IR) spectrum was recorded on an FT-IR spectrometer (IFS-66/FRA106S; Brucker, Karlsruhe, Germany). Gas chromatography-mass spectrometry (GC-MS) was performed (Agilent 6890 gas chromatograph/5973N; Agilent, Palo Alto, Calif., USA). The $^1$H NMR (500 MHz), $^{13}$C NMR (125 MHz), DEPT, HMBC, and HMQC spectra were recorded on a spectrometer (Avance 500, Bruker, Karlsruhe, Gemary), using $CD_3OD$ as a solvent.

The compound was a colorless oil; $[\alpha]^{25}_D \pm 0$ (c 0.1, methanol); UV $\lambda_{max}$ (methanol) 365 nm; IR (KBr) $v_{max}$ 3350, 2981, 1679, 1601, 1395, 1360, 1252, 1188, 1104, 921, 845, and 563 $cm^{-1}$; GC-MS m/z 160 [M]$^+$; $^1$H-NMR ($CD_3OD$, 500 MHz) and $^{13}$C NMR ($CD_3OD$, 125 MHz).

Cell Culture

SW620 and HCT116 human colon cancer cells were obtained from the American Type Culture Collection (Cryosite, Lane Cove NSW, Australia). SW620 and HCT116 human colon cancer cells were grown in RPMI1640 with 10% fetal bovine serum, 100 U/ml penicillin, and 100 μg/ml streptomycin at 37° C. in 5% $CO_2$ humidified air.

Cell Viability Assay

SW620 and HCT116 colon cancer cells were plated at a density of $10^4$ cells/well in 96-well plates per 100 μl medium. To determine the appropriate concentration that is not cytotoxic to the cells, the cytotoxic effect was evaluated in cells cultured for 12, 24, 36, and 48 h using the cell counting kit-8 assay kit according to the manufacturer's instructions (Dojindo, Gaithersburg, Md., USA). Briefly, 10 μl of the CCK-8 solution was added to cells cultured for the designated time. The plates were incubated for 1-4 h in the incubator. The resulting color was assayed at 450 nM using a microplate absorbance reader (Sunrise, Tecan, Switzerland). Each assay was carried out in triplicate.

Gel Electromobility Shift Assay

Gel shift assay was performed according to the manufacturer's recommendations (Promega, Madison, Wis., USA). Briefly, the sample of $1 \times 10^6$ cells/ml was washed twice with 1×PBS, followed by the addition of 1 ml of PBS, and the cells were scraped into a cold Eppendorf tube. Cells were pelleted by centrifugation at 15,000×g for 5 min, and the resulting supernatant was removed. Solution A (50 mM HEPES, pH 7.4, 10 mM KCl, 1 mM EDTA, 1 mM EGTA, 1 mM dithiothreitol, 0.1 μg/ml phenylmethylsulfonyl fluoride, 1 μg/ml pepstatin A, 1 μg/ml leupeptin, 10 μg/ml soybean trypsin inhibitor, 10 μg/ml aprotinin, and 0.5% Nonidet P-40) was added to the pellet in a 2:1 ratio (v/v) and allowed to incubate on ice for 10 min. Solution C (solution A+10% glycerol and 400 mM KCl) was added to the pellet in a 2:1 ratio (v/v), and vortexed on ice for 20 min. The cells were centrifuged at 15,000×g for 7 min, and the resulting nuclear extract supernatant was collected in a chilled Eppendorf tube. Consensus oligonucleotides were end-labeled using T4 polynucleotide kinase and [γ-$P^{32}$] ATP for 10 min at 37° C. Gel shift reactions were assembled and allowed to incubate at room temperature for 10 min followed by the addition of 1 μl (50,000-200,000 cpm) of $^{32}$P-labeled oligonucleotide and another 20 min of incubation at room temperature. Subsequently 1 μl of gel loading buffer was added to each reaction and loaded onto a 4% nondenaturing gel and electrophoresis was performed until the dye was three-fourths of the way down the gel. In EMSA competition studies, a 100-fold excess of unlabeled competitor oligonucleotide NF-κB was incubated with nuclear extract for 30 min before the addition of the labeled probe. The mixture with the labeled probe was incubated for another 30 min on ice. For the supershift assay, 0.5 μg of the indicated antibodies (p65 and p50) were further added, and the mixture was incubated for an additional 30 min on ice and then subjected to gel electrophoresis using 6% native polyacrylamide gels in 1×Tris-borate-EDTA buffer for 2 h. The gel was dried at 80° C. for 50 min and exposed to film overnight at −70° C. The relative density of the DNA-protein binding bands was scanned by densitometry using MyImage (SLB, Seoul, Korea), and quantified by Labworks 4.0 software (UVP Inc., Upland, Calif., USA).

Western Blot Analysis

Cultured cells were washed twice with 1×PBS, followed by the addition of 1 ml of PBS, and the cells were scraped into a cold Eppendorf tube. Cells were homogenized with lysis buffer [50 mM Tris pH 8.0, 150 mM NaCl, 0.02% sodium azide, 0.2% SDS, 1 mM PMFS, 10 μl/ml aprotinin, 1% igapel 630 (Sigma-Aldrich, St. Louis, Mo., USA), 10 mM NaF, 0.5 mM EDTA, 0.1 mM EGTA, and 0.5% sodium deoxycholate] and centrifuged at 23,000×g for 15 min. The protein concentration was measured by the Bradford method (Bio-Rad Protein Assay; Bio-Rad Laboratories Inc., Hercules, Calif., USA), and equal amount of proteins (50 μg) were separated on a SDS/12%-polyacrylamide gel and then transferred to a Hybond ECL nitrocellulose membrane (Amersham Pharmacia Biotech Inc., Piscataway, N.J., USA). Blots were blocked for 2 h at room temperature with 5% (w/v) non-fat dried milk in Tris-buffered saline [10 mM Tris (pH 8.0) and 150 mM NaCl] solution containing 0.05% tween-20. The membrane was incubated for 5 h at room temperature with specific antibodies:mouse monoclonal inducible nitric oxide synthase (iNOS) antibody (1:500), mouse polyclonal antibodies against p65 and p50 (1:500 dilution; Santa Cruz Biotechnology Inc., Santa Cruz, Calif., USA); rabbit polyclonal for cyclooxygenase (COX)-2, Bax, and Bcl-2 (1:500 dilution, Santa Cruz Biotechnology Inc.); and for caspase-3, cleaved caspase-3, cleaved caspase-9, cleaved poly (ADP-ribose) polymerase (PARP), inhibitor of apoptosis protein (cIAP) 1, and X-chromosome linked inhibitor of apoptosis protein (XIAP) (1:1000 dilution; Cell Signaling Technology, Inc., Beverly, Mass., USA). The blot was then incubated with the corresponding conjugated anti-rabbit and anti-mouse immunoglobulin G-horseradish peroxidase (1:4,000 dilution, Santa Cruz Biotechnology Inc.). Immunoreactive proteins were detected with the ECL Western blotting detection system. The relative density of the protein bands was scanned by densitometry using MyImage (SLB) and quantified by Labworks 4.0 software (UVP Inc.).

Transfection and Assay of Luciferase Activity

SW620 and HCT116 human colon cells ($2.5 \times 10^5$ cells/$cm^2$) were plated in 24-well plates and transiently transfected with pNF-κB-Luc plasmid (5×NF-κB; Stratagene, La Jolla, Calif., USA) using a mixture of plasmid and lipofectAMINE PLUS in OPTI-MEN according to manufacturer's specifications (Invitrogen, Carlsbad, Calif., USA). The transfected cells were treated with tumor necrosis factor-α (TNF-α) (10 ng/ml) or TPA (50 nM) and different concentrations (30-150 μg/ml) of thiacremonone for 8 h. Luciferase activity was measured by using the luciferase assay kit (Promega, Madison, Wis., USA) according to the manufacturer's instructions (WinGlow, Bad Wildbad, Germany).

Detection of Apoptosis

Apoptosis assay was first performed by using 4,6-diamino-2-phenylindole (DAPI) staining. SW620 and HCT116 human colon cancer cells were cultured in the absence or presence of increasing concentrations of thiacremonone, and induction of apoptotic cell death was evaluated after 24 h. Apoptotic cells were determined by the morphological changes after DAPI staining under fluorescence microscopic observation (DAS microscope, 100× or 200×: Leica Microsystems, Inc., Deefield, Ill., USA). Apoptosis was also evaluated by TUNEL staining assay. In short, cells were cultured on 8-chamber slides. After treatment with thiacremonone (30-150 μg/ml) for 24 h, the cells were washed twice with PBS and fixed by incubation in 4% paraformaldehyde in PBS for 1 h at room temperature. TUNEL assays were performed by using the in situ Cell Death Detection Kit (Roche Diagonostics GmbH, Mannheim, Germany) according to manufacturer's instructions. Total number of cells in a given area was determined by using DAPI and TUNEL staining. The apoptotic index was determined as the number of DAPIstained TUNEL-positive cells divided by the total cell number counted ×100.

Data Analyses

Statistical analyses of data were performed by using one-way analysis of variance followed by the Tukey test as a post hoc test. Differences were considered significant at $P<0.05$.

Results

Antioxidant Activity of the Solvent Fraction and Isolation of the Active Compound from Heated Garlic The optimum heating condition for garlic was previously determined as 130° C. for 2 hr (13). The active compound was isolated from HGJ exposed to 120° C., 130° C., and 140° C. for 2 hr and successively fractionated with hexane, chloroform, ethyl acetate, butanol, and water. Chemical assays were used based on the ability of the compound to scavenge model free radicals, i.e., DPPH and ABTS radicals, because of their simplicity and worldwide acceptance for comparative purposes. The antioxidant activity of the ethyl acetate fraction was higher than that of the hexane, chloroform, butanol, and water fractions. The ethyl acetate fraction of HGJ treated at 130° C. for 2 hr showed strong antioxidant activity compared with those from the other heating conditions. Therefore, we isolated and purified the active compound from the ethyl acetate fraction of HGJ treated at 130° C. for 2 hr.

The 4.8 g ethyl acetate fraction of 2 kg of heated garlic exposed to 130° C. for 2 hr was subjected to activity-guided repeated fractionation on a silica gel column and eluted with an increasing concentration of methanol in dichloromethane. Silica gel chromatography resulted in one active fraction, A1 (1.6 g; data not shown). The active fraction A1 was repurified using silica gel chromatography (dichloromethane:methanol) to obtain three active fractions, B4-B6 (0.26 g; data not shown). We then attempted to isolate the active compound from the B4-B6 fractions using semi-preparative HPLC on a C18 column. The chemical structure of the isolated compound was determined using spectroscopic methods.

Identification of the Isolated Compound

The compound obtained was a colorless oil. The GC-MS spectrum showed a molecular ion peak at m/z 160, corresponding to a molecular formula of $C_6H_8O_3S$. The UV and IR spectra of the compound indicated the presence of an α,β-unsaturated ketone, substituted with an oxygen in the α position and a sulfur in the β position (20). The $^1H$ NMR spectrum of the compound showed signals assignable to two quaternary methyl groups at d 1.63 and d 2.18. The $^{13}C$ NMR and DEPT spectra confirmed that the molecule contained six carbon atoms consisting of two methyl groups at d 14.9 and d 27.1, two olefinic carbons at d 139.8 and d 148.3, a ketone signal at d 199.1, and a quaternary oxygen-bearing carbon at d 85.7. This indicates that the compound has a 3-thiphenone ring. The two methyl groups were located at C-2 and C-5, based on HMBC correlations between the methyl signals at d 1.63 and d 85.7 (C-2) and d 199.1 (C-3), as well as between the other methyl signals at d 2.18 and d 148.3 (C-4) and d 138.8 (C-5).

Therefore, the isolated active compound from HGJ treated at 130° C. for 2 hr was identified as thiacremonone(2,4-dihydroxy-2,5-dimethyl-thiophene-3-one) by comparing its physicochemical and spectroscopic data with those from the literature (31). According to the HPLC analysis, the thiacremonone of raw garlic juice was not detected. Thiacremonone has been also isolated from the fungus *Acremonium* sp. strain HA33-95 and identified as an inducer of differentiation in mammalian cells (31).

Chemicals

A chemical compound (named thiacremonone) isolated from heated garlic was characterized and found to be the same as the compound isolated from *Acremonium* sp. strain HA33-95 fermentation as described by Gehrt et al. (31). The structure is shown as follows.

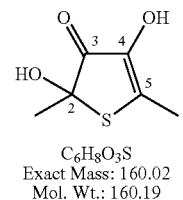

$C_6H_8O_3S$
Exact Mass: 160.02
Mol. Wt.: 160.19

Thiacremonone was dissolved in 0.1% DMSO and used at the treatment dose of 30-150 μg/ml.

Thiacremonone Inhibited NF-κB Activation

Figure 1B:
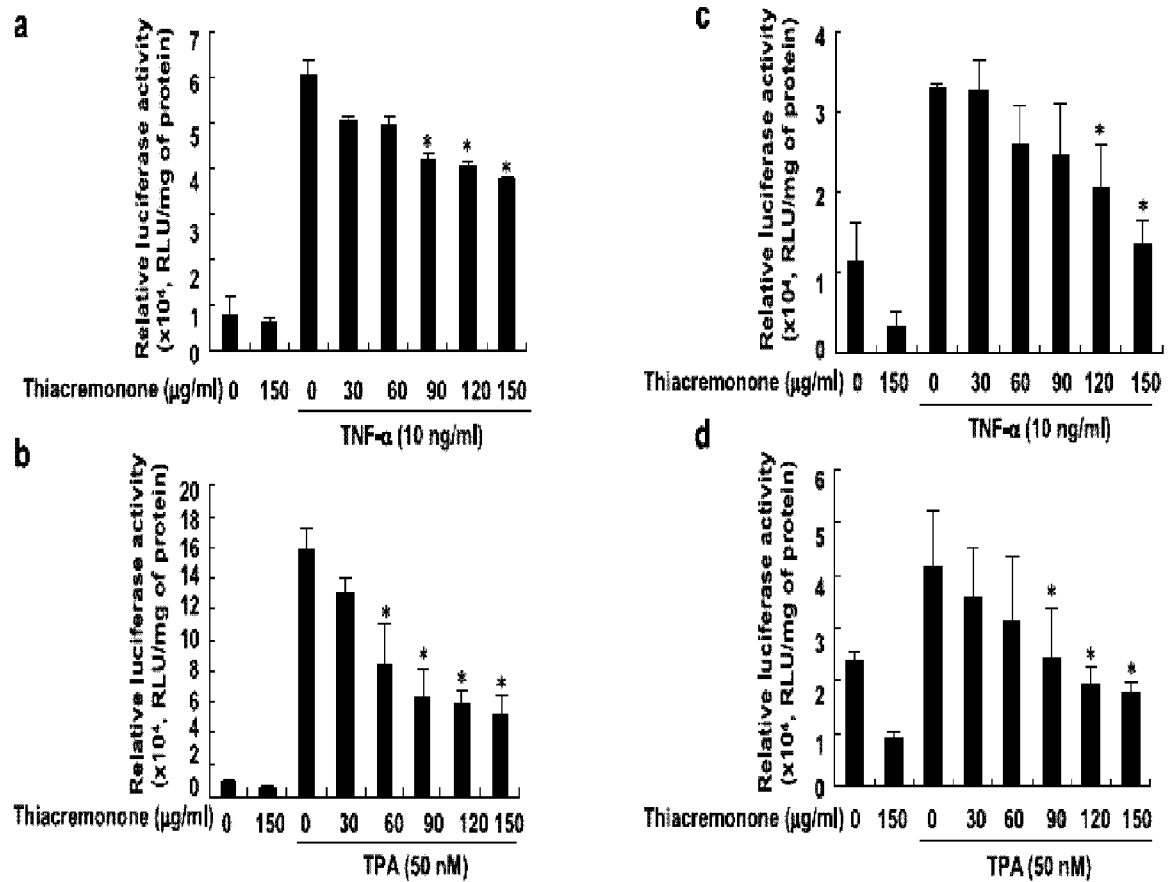

NF-κB is a factor implicated in apoptotic cell death of several types of cancer cells. To determine whether inactivation of NF-κB may be also involved in thiacremonone-induced apoptotic cell death, we determined DNA binding activity of NF-κB by the electrophoretic gel mobility shift assay. We found that high DNA binding activity of NF-κB was detected in the untreated SW620 and HCT116 colon cancer cells, and thiacremonone decreased DNA binding activity of NF-κB in a dose-dependent manner (30-150 μg/ml) in both SW620 (FIG. 1A panel a) and HCT116 colon cancer cells (FIG. 1A panel b). This NF-κB DNA binding activity was confirmed by competition assay using unlabelled NF-κB as well as by super shift assay using antibody treatment of NF-κB subunits (p65 and p50). The supershift result indicated that p65 subunit is major target of thiacremonone (FIG. 1A panel c).

To determine the effect of thiacremonone on TNF-α-induced NF-κB-dependent reporter gene expression, we transiently transfected the cells with a NF-κB-regulated luciferase reporter construct, and then the transfected cells were stimulated with TNF-α alone or the combination of TNF-α and thiacremonone. Consistent with the inhibitory effect on NF-κB DNA binding activity, thiacremonone (30-150 μg/ml) inhibited TNF-α and TPA induced NF-κB luciferase activity dose-dependently in both SW620 (FIG. 1B panel a and b) and HCT116 (FIG. 1B panel c and d) colon cancer cells.

Thiacremonone Inhibited in SW620 and HCT116 Human Colon Cancer cell growth

To investigate the inhibitory effect of thiacremonone on SW620 and HCT116 human colon cancer cell growth, we analyzed cell growth by the CCK-8 assay. Morphological observation showed that the cells gradually reduced in size and changed to a round single cell shape in a dose-dependent manner by the treatment with thiacremonone in both SW620 (FIG. 2A panel a) and HCT116 (FIG. 2B panel a) colon cancer cells. Cancer cell growth inhibitory effects were dose-dependent (30-150 μg/ml) in both SW620 (FIG. 2A panel b) and HCT116 (FIG. 2B panel b) human colon cancer cells. $IC_{50}$ values (48 h) of cell growth inhibition were $10^5$ μg/ml in SW620 colon cancer cells and 130 μg/ml in HCT116 colon cancer cells.

However, thiacremone showed no cytotoxic effect in the normal colon Caco-2 cells (FIG. 2C panel a and b).

Thiacremonone Induced Apoptotic Cell Death

To determine whether the inhibition of cell growth by thiacremonone was due to the induction of apoptotic cell death, we evaluated changes in the chromatin morphology of cells using DAPI staining. To further characterize the apoptotic cell death by thiacremonone, we performed TUNEL staining assays, and then the labeled cells were analyzed by fluorescence microscopy. Thiacremonone-treated cells were labeled by TUNEL assay and there was increased fluorescence intensity in both SW620 (FIG. 3A panel a) and HCT116 (FIG. 3A panel b) colon cancer cells.

In SW620 colon cancer cells, the apoptotic cell number (DAPI-positive TUNEL-stained cells) was increased to 0%, 0%, 11%, 25%, and 97% by 30, 60, 90, 120, and 150 μg/ml thiacremonone, respectively (FIG. 3B panel a). In HCT116 colon cancer cells, the apoptotic cell number was increased to 0%, 0%, 29%, 95%, and 98% by 30, 60, 90, 120, and 150 μg/ml thiacremonone, respectively (FIG. 3B panel b).

Thiacremonone Induced the Expression of Apoptotic Regulatory Proteins

NF-κB can regulate genes controlling apoptotic cell death. NF-κB activation in colon cancer cells correlates with resistance to apoptosis and increased levels of antiapoptotic proteins. Anticancer drugs are considered to mediate cell death by activating key elements of the apoptosis program relating NF-κB. To figure out the relationship between the induction of apoptosis by thiacremonone and expression of NF-κB target apoptotic gene expression, expressions of apoptosis-related proteins were investigated. Expressions of apoptotic proteins such as Bax, cleaved caspases 3, and cleaved PARP were increased, whereas the expressions of antiapoptotic protein Bcl-2, cIAP1/2, XIAP, and cell cycle regulating gene cyclin D1 were decreased. We also found that iNOS and COX-2 expression was high in these colon cancer cell lines, but thiacremonone treatment inhibited the expressions dose-dependently in both SW620 (FIG. 4 panel a) and HCT116 (FIG. 4 panel b) colon cancer cells.

Thiacremonone Inhibited Growth of Colon Cancer Cell Growth in vivo Xenograft.

To elucidate the anticancer effect of thiacremonone in vivo, the tumor growth on colon xenograft bearing nude mice following thiacremonone treatments were investigated. In SW620 xenograft studies, thiacremonone was administrated intraperitoneally twice per week for 4 weeks to mice with tumors ranging from 100 to 300 mm3 of tumor volume. The mice were weighted twice per week. The change of body weights between saline and thiacremonone-administrated mice (n=10) was not different during the experiment.

FIG. 5 represents the relative tumor growth delay measured after treatment of thiacremonone (240 and 360 mg/kg for four weeks, n=10) in comparison with the sham control group (saline). By day 31, tumor volume in mice treated with thiacremonone 240 mg/kg and 360 mg/kg were reduced to 92.5% and 59.1% of sham control group, respectively. These results suggested that in agree with in vitro, thiacremonone suppressed cancer cell growth in vivo.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating colon cancer, which comprises administering to a subject suffering from colon cancer a pharmaceutical composition comprising (a) a pharmaceutically effective amount of thiacremonone that is isolated from fractions exhibiting anti-oxidant activities fractionated from heated *Allium sativum* L and purified with column chromatography and preparative HPLC; and (b) a pharmaceutically acceptable carrier.

* * * * *